United States Patent
Barr et al.

(10) Patent No.: US 6,258,566 B1
(45) Date of Patent: *Jul. 10, 2001

(54) PRODUCTION OF POLYKETIDES IN BACTERIA AND YEAST

(75) Inventors: Philip J. Barr, Oakland; Daniel V. Santi, San Francisco; Gary W. Ashley, Alameda; Rainer Ziermann, San Mateo, all of CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/422,073

(22) Filed: Oct. 21, 1999

Related U.S. Application Data

(63) Continuation of application No. 08/989,332, filed on Dec. 11, 1997, now Pat. No. 6,033,883.
(60) Provisional application No. 60/033,193, filed on Dec. 18, 1996.

(51) Int. Cl.[7] .................................................. C12P 19/62
(52) U.S. Cl. .................... 435/76; 435/252.3; 435/254.11; 435/419; 435/325; 435/252.33; 435/254.2; 435/252.6; 435/320.1; 435/183
(58) Field of Search ................................ 435/410, 252.3, 435/320.1, 252.33, 254.2

(56) References Cited

U.S. PATENT DOCUMENTS

| | | |
|---|---|---|
| 5,672,491 | 9/1997 | Khosla et al. . |
| 5,712,146 | 1/1998 | Khosla et al. . |
| 5,744,350 | 4/1998 | Vinci et al. . |

(List continued on next page.)

FOREIGN PATENT DOCUMENTS

| | | |
|---|---|---|
| WO95/12661 | 5/1995 | (WO) . |
| WO95/33818 | 12/1995 | (WO) . |

(List continued on next page.)

OTHER PUBLICATIONS

Carrcaras et al., *Biochemistry*, 36(39):11757–11761 (Nov. 1997).
Cox et aal., FEBS Letters, 405(3):267–272 (Mar. 1997).
Fujii et al., *Molecular and General Genetics*, 253(1):1–10 (Nov. 1996).
Roberts et al., *European J. of Biochem.*, 214:305–311 (Mar. 1993).
Crosby et al. Polyketide synthase acyl carrier proteins from Streptomyces: Expression in *Escherichia coli*, purification and partial characterisation. Biochimica et Biophysica Acta 1251:32–42, Aug. 1995.
Shen et al. Purification and Characterization of the Acyl Carrier Protein of the *Streptomyces glaucescens* Tetracenomycin C Polyketide Synthase. J. of Bacteriology 174(11):3818–3821, Jun. 1992.

(List continued on next page.)

*Primary Examiner*—Ponnathapu Achutamurthy
*Assistant Examiner*—Kathleen Kerr
(74) *Attorney, Agent, or Firm*—Kevin Kaster, Esq.; Kate Murashige, Esq.; Carolyn Favorito, Esq.

(57) ABSTRACT

Hybrid and novel polyketide synthases (PKSs) and polyketides are produced by use of a multiple vector system. The combinatorial possibilities offered by placing the various catalytic activities of PKS systems on separate vectors permits the construction of improved libraries of PKS and polyketides. In addition, polyketides can be produced in hosts that ordinarily do not produce polyketides by supplying, along with an expression system for the desired PKS, an expression system for holo acyl carrier protein (ACP) synthase.

17 Claims, 7 Drawing Sheets

U.S. PATENT DOCUMENTS

| | | |
|---|---|---|
| 5,824,513 | 10/1998 | Katz et al. . |
| 5,830,750 | 11/1998 | Khosla et al. . |
| 5,843,718 | 12/1998 | Khosla et al. . |
| 5,962,290 | 10/1999 | Khosla et al. .................. 435/183 |
| 6,080,555 | 6/2000 | Khosla et al. .................. 435/41 |

FOREIGN PATENT DOCUMENTS

| | | |
|---|---|---|
| WO97/13845 | 4/1997 | (WO) . |
| WO99/02669 | 1/1999 | (WO) . |

OTHER PUBLICATIONS

Shen et al. Enzymatic Synthesis of a Bacterial Plyketide from Acetyl and Malonyl Coenzyme A. Science 262:1535–1540, Dec. 1993.

Gramajo et al. Overproduction and Localization of Compounds of the Polyketide Synthase of *Streptomyces glucescens* Involved in the Production of the Antibiotic Tetracenomycin C. J. of Bacteriology 173(20):6475–6483, Oct. 1991.

Roberts et al. Heterologous expression in *Escherichia coli* of an intact multienzyme component of the erythromycin–producing polyketide synthase. European J. of Biochemistry 214:305–311, May 1993.*

Lambalot et al. Cloning, Overproduction and Characterization of the *Escherichia coli* Holo–acyl Carrier Protein Synthase J. of Biological Chemistry 270(42):24658–26441, Oct. 1995.*

Oliynyk et al. A hybrid modular polyketide synthase obtained by domain swapping. Chemistry & Biology 3:833–839, Oct. 1996.*

Lambalot et al., A new enzyme superfamily—the phosphopantetheinyl transferases. Chemistry & Biology 3:923–936, Sep. 1996.*

Bierman et al. Plasmid cloning vectors for the conjugal transfer of DNA from *Escherichia coli* to *Streptomyces spp.* Gene (1992) 116:43–49.*

* cited by examiner

ARRANGEMENT OF DOMAINS WITHIN THE 6-MSAS GENE.

SPIRAMYCIN 2 MODULE SYSTEM

ERYTHROMYCIN 2 MODULE SYSTEM

SEQUENCE LISTING

<160> NUMBER OF SEQ ID NOS: 7

<210> SEQ ID NO: 1
<211> LENGTH: 40
<212> TYPE: DNA
<213> ORGANISM: Artificial Sequence
<220> FEATURE:
<223> OTHER INFORMATION: Primer

<400> SEQUENCE: 1
gggagctcgg atccatttag cggccgcaaa acgtaggggc          40

<210> SEQ ID NO: 2
<211> LENGTH: 44
<212> TYPE: DNA
<213> ORGANISM: Artificial Sequence
<220> FEATURE:
<223> OTHER INFORMATION: Primer

<400> SEQUENCE: 2
ccgaattcta gaggtttcat atggtattac gatatagtta atag          44

<210> SEQ ID NO: 3
<211> LENGTH: 43

```
<212> TYPE: DNA
<213> ORGANISM: Artificial Sequence
<220> FEATURE:
<223> OTHER INFORMATION: Primer

<400> SEQUENCE: 3
gggaattcat agtcgaccgg accgatgcct tcacgattta tag         43

<210> SEQ ID NO: 4
<211> LENGTH: 42
<212> TYPE: DNA
<213> ORGANISM: Artificial Sequence
<220> FEATURE:
<223> OTHER INFORMATION: Primer

<400> SEQUENCE: 4
ttttctatta taagatgaaa aacgagggga gctcccatgg cc          42

<210> SEQ ID NO: 5
<211> LENGTH: 33
<212> TYPE: DNA
<213> ORGANISM: Artificial Sequence
<220> FEATURE:
<223> OTHER INFORMATION: Primer

<400> SEQUENCE: 5
tagacacata tgaagattta cggaattttat atg                   33

<210> SEQ ID NO: 6
<211> LENGTH: 29
<212> TYPE: DNA
<213> ORGANISM: Artificial Sequence
<220> FEATURE:
<223> OTHER INFORMATION: Primer

<400> SEQUENCE: 6
tacattctag aaattataaa agctcttcg                         29

<210> SEQ ID NO: 7
<211> LENGTH: 33
<212> TYPE: DNA
<213> ORGANISM: Artificial Sequence
<220> FEATURE:
<223> OTHER INFORMATION: Primer

<400> SEQUENCE: 7
aagcttgcca aagccgccgc catgaagatt tac                    33
```

PRODUCTION OF POLYKETIDES IN BACTERIA AND YEAST

This application claims priority under 35 USC 119 from provisional application 60/033,193 filed Dec. 18, 1996. The contents of this provisional application are incorporated herein by reference.

This application is a continuation of U.S. patent application Ser. No. 08/989,332, filed Dec. 11, 1997, which issued Mar. 7, 2000, as U.S. Pat. No. 6,033,883, and is incorporated by reference herein.

TECHNICAL FIELD

The invention relates to production of polyketides in microbial hosts such as yeast and *E. coli* and to preparation of libraries containing a variety of functional polyketide synthases (PKSs) and the resulting variety of polyketides. More specifically, it concerns supplying portions of the polyketide synthase systems on separate vectors for simplicity in mixing and matching these portions to create a variety of PKS. This permits production of libraries of polyketide syntheses and polyketides through a combinatorial approach rather than manipulation focused on a single production system.

BACKGROUND ART

Polyketides represent a singularly useful group of natural products which are related by their general pathway of biosynthesis. Representative members include the macrolide antibiotics, for example, erythromycin, spiramycin and tylosin, immunosuppressants such as rapamycin and FK506, antiparasitics such as the avermectins, antifungal agents such as amphotericin B and nystatin, anticancer agents such as daunorubicin and doxorubicin and anticholesterolemics such as mevinolin. Polyketides generally are secondary metabolites of the actinomycetes including the genera Streptomyces, Actinomyces, Actinomadura, Micromonospora, Saccharopolyspora, and Nocardia. It was estimated that in 1986 about 6,000 antibiotics of microbial origin had been characterized of which 70 were in clinical use; an additional 1100 metabolites were reported between 1988 and 1992, approximately 40% of which were polyketides.

Despite the multiplicity of polyketide structures available from nature, there remains a need to expand the repertoire of available polyketides and to synthesize a multiplicity of polyketides in the form of libraries so that there is a convenient substrate for screening to identify polyketides that are relevant to a specific target of interest. The present invention provides solutions to these needs.

Polyketides generally are synthesized by condensation of two-carbon units in a manner analogous to fatty acid synthesis. In general, the synthesis involves a starter unit and extender units; these "two-carbon" units are derived from acylthioesters, typically acetyl, propionyl, malonyl or methylmalonyl coenzyme-A thioesters. There are two major classes of polyketide synthases (PKSs) which differ in the "manner" in which the catalytic sites are used—the so-called "aromatic" PKS and the modular PKS. The present invention employs coding sequences from both these classes as will further be explained below.

Recombinant production of heterologous functional PKS—i.e., a PKS which is capable of producing a polyketide—has been achieved in Streptomyces and hybrid forms of aromatic PKSs have been produced in these hosts as well. See, for example, Khosla, C. et al. *J Bacteriol* (1993) 175:2194–2204; Hopwood, D. A. et al. *Nature* (1985) 314:642–644; Sherman, D. H. et al. *J Bacteriol* (1992) 174:6184–6190. In addition, recombinant production of modular PKS enzymes has been achieved in Streptomyces as described in PCT application WO 95/08548. In all of these cases, the PKS enzymes have been expressed from a single vector. A single vector which carried genes encoding PKS catalytic sites was transformed into *E. coli* by Roberts, G. A., et al., *Eur J Biochem* (1993) 214:305–311, but the PKS was not functional, presumably due to lack of pantetheinylation of the acyl carrier proteins.

The present invention provides double or multivector systems for production of PKS and the resultant polyketides in a variety of hosts. The use of multiple vectors provides a means more efficiently to enhance the number of combinatorial forms of PKS and polyketides that can be prepared. Addition of the machinery for pantetheinylation of the acyl carrier proteins (i.e., a holo ACP synthase) permits production of polyketides in a wide spectrum of hosts.

DISCLOSURE OF THE INVENTION

The invention relates to recombinant materials for the production of polyketides in a wide variety of hosts and of libraries of PKS enzymes and the resultant polyketides based on a multiple vector system. The use of a multivector system facilitates the construction of combinatorial libraries and permits more flexibility in designing various members thereof. The invention also relates to such libraries which are essentially self-screening due to an autocrine system involving polyketide-responsive receptors.

Thus, in one aspect, the invention relates to a recombinant host cell and libraries thereof when the host cell is modified to contain at least two vectors, a first vector containing a first selection marker and a first expression system and the second vector containing a second selection marker and a second expression system and optionally additional vectors containing additional selectable markers and expression systems, wherein the expression systems contained on the vectors encode and are capable of producing at least a minimal PKS system. If the minimal PKS system is an aromatic system, the minimal system will comprise a ketosynthase/acyl transferase (KS/AT) catalytic region, a chain length factor (CLF) catalytic region and an acyl carrier protein (ACP) activity. If the minimal PKS system is a modular system, the system will contain at least a KS catalytic region, an AT catalytic region, and an ACP activity. For modular systems, these activities are sufficient provided intermediates in the synthesis are provided as substrates; if de novo synthesis is to be required, a loading acyl transferase should be included, which will include another AT and ACP region.

In one specific embodiment of this aspect of the invention, the recombinant host cell will be modified to contain: (a) a first vector comprising a first selectable marker and an expression system comprising a nucleotide sequence encoding a ketosynthase/acyl transferase (KS/AT) catalytic region of an aromatic PKS operably linked to a promoter operable in said cell; (b) a second vector comprising a second selectable marker and an expression system comprising a nucleotide sequence encoding a chain length factor (CLF) catalytic domain operably linked to a promoter operable in said cell; and (c) a third vector containing a third selectable marker and an expression system which comprises a nucleotide sequence encoding an acyl carrier protein (ACP) activity operably linked to a promoter operable in said cell, and to libraries comprised of colonies of such cells.

Alternatively, two of the vectors can be combined so that the host cell contains only two vectors; the vector containing two expression systems may maintain these as separate expression systems or two open reading frames may be placed under the control of a single promoter.

In another specific embodiment, the invention relates to a cell modified to contain a first vector containing a first selectable marker and an expression system for at least one minimal module of a modular polyketide synthase (PKS) operably linked to a promoter operable in said cell; and a second vector containing a second selectable marker and a nucleotide sequence encoding at least a second minimal module of a modular polyketide synthase operably linked to a promoter operable in said cell, and to libraries comprising colonies of such cells.

In another variation, one or more expression systems for a defined portion of a PKS system is integrated into the host chromosome and at least one additional expression system resides on a replicable vector. Thus, in the case of aromatic PKS, an expression system for one of the open reading frames may first be integrated into the chromosome and expression systems for other open reading frames may reside on vectors. In the case of a modular PKS, an expression system for one or more modules may reside on the chromosome and additional expression systems for one or more modules reside on vectors. The integration of such expression systems into the chromosome can occur either through known phage-mediated integration or by homologous recombination.

The invention also is directed to novel polyketides produced by the methods of the invention and to methods to screen the polyketide libraries obtained.

In still another aspect, the invention is directed to methods to obtain the synthesis of polyketides in hosts that lack a mechanism for activation of the acyl carrier proteins—i.e., which lack holo ACP synthases. By supplying an expression system for a compatible holo ACP synthase either on a separate vector, on one of the vectors in a multiple vector system (or on a single vector for PKS expression), or as a fusion protein with a PKS or portion thereof, hosts such as *E. coli*, yeast, and other microbial systems which do not customarily synthesize polyketides can be made into convenient hosts. This obviates the necessity for supplying "clean" hosts from polyketide-producing strains of, for example, Streptomyces.

MODES OF CARRYING OUT THE INVENTION

Figure 1:
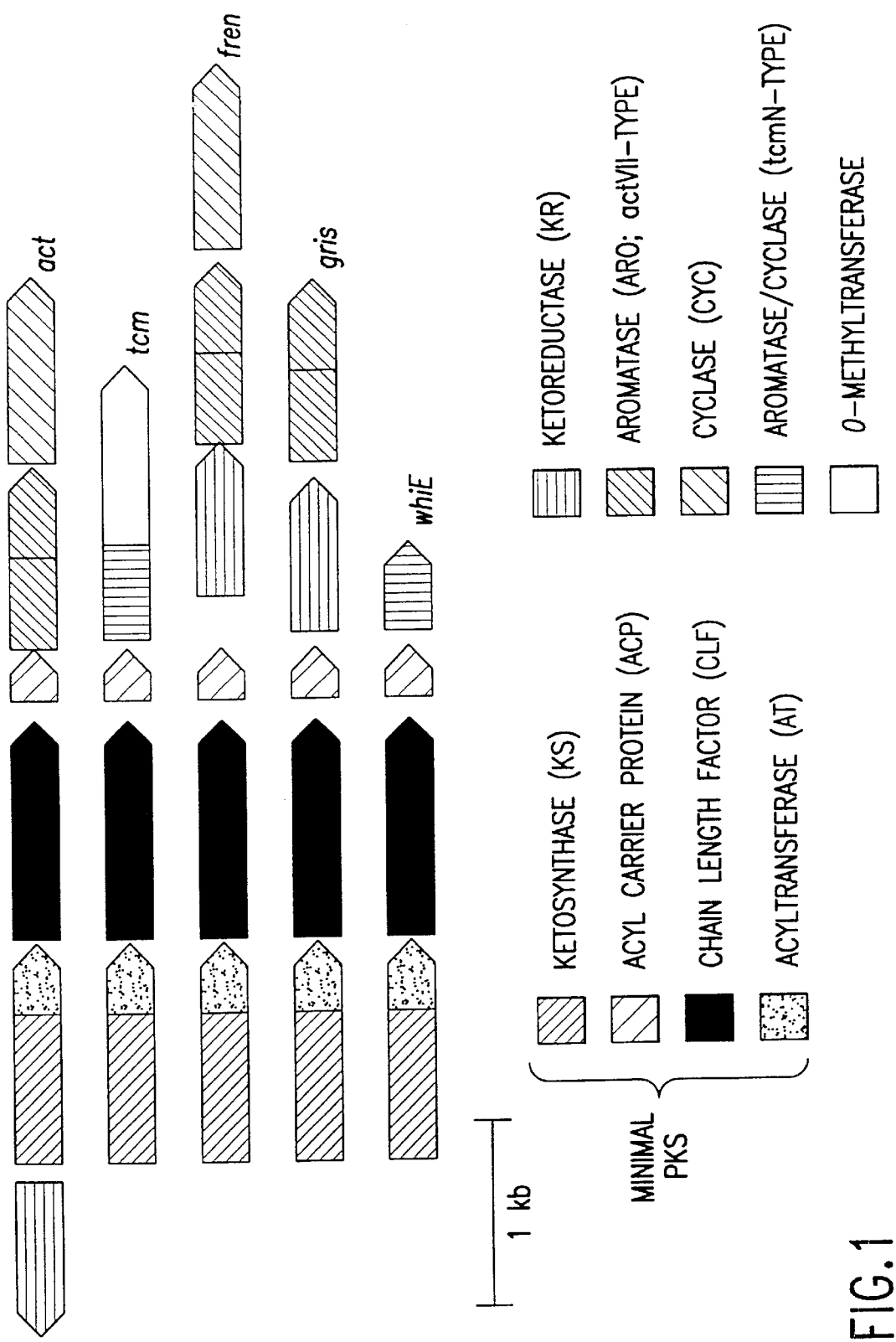
FIG. 1 is a diagram showing the composition of several typical aromatic PKS.
Figure 2:
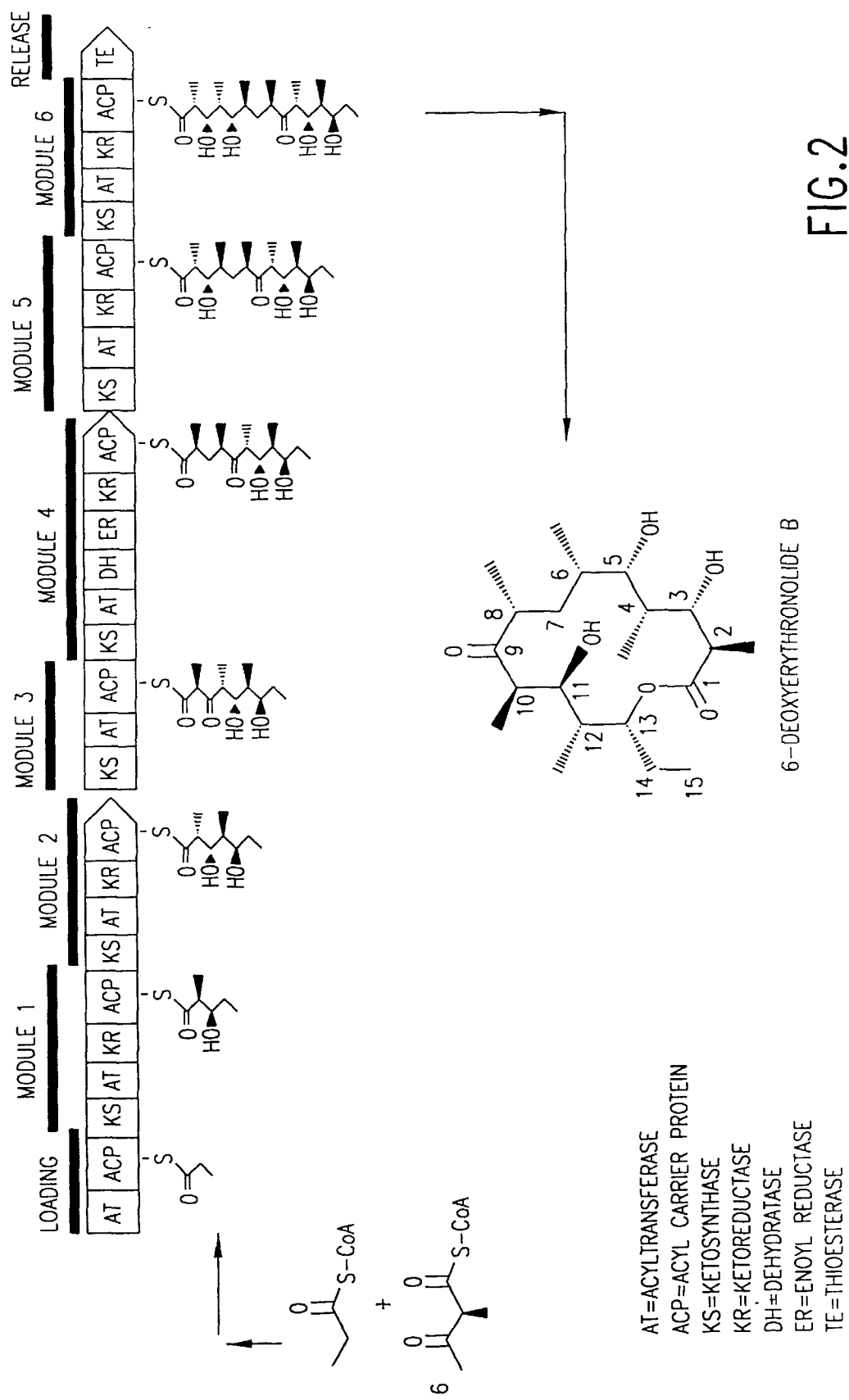
FIG. 2 is a diagram showing the organization of erythromycin PKS as typical of a modular PKS.
Figure 3:
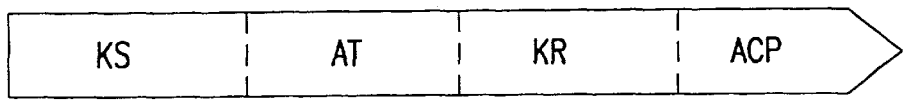
FIG. 3 is a diagram showing the organization of the fungal PKS system, 6-methyl salicylic acid synthase (6-MSAS).

The invention in various aspects employs various components of the aromatic, PKS system, the modular PKS system, a fungal PKS system, or modified forms thereof or portions of more than one of these. The general features of aromatic, modular and fungal PKS systems are shown in FIGS. 1, 2 and 3 respectively.

"Aromatic" PKS systems are characterized by the iterative use of the catalytic sites on the several enzymes produced. Thus, in aromatic PKS systems, only one enzyme with a specific type of activity is produced to catalyze the relevant activity for the system throughout the synthesis of the polyketide. In aromatic PKS systems, the enzymes of the minimal PKS are encoded in three open reading frames (ORFs). As shown in FIG. 1, the actinorhodin PKS is encoded in six separate ORFs. For the minimal PKS, one ORF contains a ketosynthase (KS) and an acyltransferase (AT); a second ORF contains what is believed to be a chain-length factor (CLF); and a third reading frame encodes an acyl carrier protein (ACP). Additional ORFs encode an aromatase (ARO), a cyclase (CYC), and a ketoreductase (KR). The combination of a KS/AT, ACP, and CLF constitutes a minimal PKS, since these elements are necessary for a single condensation of a two-carbon unit.

On the other hand, the griseusin PKS contains five separate ORFs wherein the KS/AT, CLF, and ACP are on three ORFs, the KR is on a fourth, and the ARO is on a fifth.

In the "modular" PKS systems, each catalytic site is used only once and the entire PKS is encoded as a series of "modules." Thus, the modular synthase protein contains a multiplicity of catalytic sites having the same type of catalytic activity. A minimal module contains at least a KS, an AT and an ACP. Optional additional activities include KR, DH, an enoylreductase (ER) and a thioesterase (TE) activity. FIG. 2 shows, diagrammatically, the organization of the modular PKS system for the synthesis of the immediate-precursor, 6-dEB, for the antibiotic erythromycin. As shown, there is a loading region followed by six modules; the thioesterase on module 6 effects release of the completed 6-deoxyerythronolide B (6-dEB) from the synthase to which it is coupled through a phosphopantetheinyl group. The diagram shows the progressive formation of the 6-deB which is cyclized after removal from the holo ACP on module 6 of the synthase. To convert 6-dEB to erythromycin A, two sugar residues are added in subsequent reactions through the hydroxyl groups at positions 3 and 5.

The "fungal" PKS encoding 6-methyl salicylic acid synthase (6-MSAS) has some similarity to both the aromatic and modular PKS. It has only one reading frame for KS, AT, a dehydratase (DH), KR and ACP. Thus, it looks similar to a single module of a modular PKS. These sites are, however, used iteratively. Unlike an aromatic PKS, it does not include a CLF, as shown in FIG. 3.

The invention herein employs expression systems for the catalytic activities involved in all of the aromatic, modular and fungal PKS systems. The proteins produced may contain the native amino acid sequences and thus the substrate specificities and activities of the native forms, or altered forms of these proteins may be used so long as the desired catalytic activity is maintained. The specificity and efficiency of this activity may, however, differ from that of the native forms. Certain activities present in the native system, however, can be intentionally deleted. Further, components of various aromatic systems can be mixed and matched, as well as can components of various modules of the module systems. PCT application WO 95/08548, referenced above and incorporated herein by reference describes the construction of hybrid aromatic PKS systems where, for example, open reading frames of actinorhodin are included in expression vectors with open reading frames from alternative aromatic systems.

Expression systems for the PKS proteins alone may not be sufficient for actual production of polyketides unless the recombinant host also contains holo ACP synthase activity which effects pantetheinylation of the acyl carrier protein. This activation step is necessary for the ability of the ACP to "pick up" the "2C" unit which is the starter unit or the growing polyketide chain in the series of Claisen condensations which result in the finished polyketide. For hosts lacking a phosphopantetheinylating enzyme that behaves as a holo ACP synthase, the invention provides means for conferring this activity by supplying suitable expression systems for this enzyme. The expression system for the holo ACP synthase may be supplied on a vector separate from that carrying a PKS unit or may be supplied on the same vector or may be integrated into the chromosome of the host, or may be supplied as an expression system for a fusion protein with all or a portion of a polyketide synthase. In general, holo ACP synthases associated with fatty acid synthesis are not suitable; rather, synthases associated specifically with polyketide synthesis or with synthesis of nonribosomal proteins are useful in this regard.

Specifically, the modular and fungal PKS systems are not activated by phosphopantetheinylation effected by the phosphopantetheinylation enzymes endogenous to $E.$ $coli$; however, enzymes derived from Bacillus, in particular the gramicidin holo ACP synthase of $Bacillus$ $brevis$ and the surfactin-related holo-ACP synthase from $Bacillus$ $subtilis$ can utilize the modular and fungal PKS ACP domains as substrates. As shown in the Examples below, while inclusion of an expression system for an appropriate holo-ACP synthase is not necessary for just the expression of the genes encoding fungal or modular PKS in $E.$ $coli$ or yeast, inclusion of such expression systems is required if polyketides are to be produced by the enzymes produced.

It should be noted that in some recombinant hosts, it may also be necessary to activate the polyketides produced through postsynthesis modifications when polyketides having antibiotic activity are desired. If this is the case for a particular host, the host will be modified, for example by transformation, to contain those enzymes necessary for effecting these modifications. Among such enzymes, for example, are glycosylation enzymes.

The combinatorial possibilities for synthesis of aromatic PKS systems depend on the nature of the iteratively used sites and the presence or absence of the optional activities that are not part of the minimal PKS system required for the Claisen condensation which represents the synthetic mechanism for the end-product polyketide. Thus, while the aromatic PK synthase must contain a KS/AT, ACP and CLF, the other catalytic activities, i.e. KR, ARO, and CYC are optional. Fungal PK synthases require only KS, AT, and ACP functionalities, as do the modular PKS systems. Various combinations of these activities from various sources can be used as well as their mutated forms.

Because the catalytic sites are used only once in the modular PKS systems, the combinatorial possibilities in this type of synthase are greater. The combinatorial potential of a modular PKS is given by: $AT_L \times (AT_E \times 4)^M$ where $AT_L$ is the number of loading acyl transferases, $AT_E$ is the number of extender acyl transferases, and M is the number of modules in the gene cluster. The number 4 is present in the formula because this represents the number of ways a keto group can be modified by either 1) no reaction; 2) KR activity alone; 3) KR+DH activity; or 4) KR+DH+ER activity. It has been shown that expression of only the first two modules of the erythromycin PKS resulted in the production of a predicted truncated triketide product. See Kao, et al. $J$ $Am$ $Chem$ $Soc$ (1994) 116:11612–11613. A novel 12-membered macrolide similar to methymycin aglycone was produced by expression of modules 1–5 of this PKS in $S.$ $coelicolor$. See Kao, C. et al. $J$ $Am$ $Chem$ $Soc$ (1995) 117:9105–9106. This work, as well as that of Cortes, J. et al $Science$ (1995) 268:1487–1489, shows that PKS modules are functionally independent so that lactone ring size can be controlled by the number of modules present.

In addition to controlling the number of modules, the modules can be genetically modified, for example, by the deletion of a ketoreductase domain as described by Donadio, S. et al. $Science$ (1991) 252:675–679; Donadio, S. et al. $Gene$ (1992) 115:97–103. In addition, the mutation of an enoyl reductase domain was reported by Donadio, S. et al. $Proc$ $NatJ$ $Acad$ $Sci$ $USA$ (1993) 90:7119–7123. These modifications also resulted in modified PKS and thus modified polyketides.

As stated above, in the present invention, the coding sequences for catalytic activities derived from the aromatic, fungal or modular PKS systems found in nature can be used in their native forms or modified by standard mutagenesis techniques to delete or diminish activity or to introduce an activity into a module in which it was not originally present. For example, a KR activity can be introduced into a module normally lacking that function.

While the art, as set forth above, has succeeded in producing some novel polyketides by virtue of construction of hybrid and/or altered aromatic or modular PKS systems in Streptomyces from a single expression vector, advantage has not been taken of using a multiple vector system in host cells generally in order to produce a wider variety of synthases. By "multiple" is meant two or more; by "vector" is meant a nucleic acid molecule which can be used to transform host systems and which contains both a selectable marker and an independent expression system containing a coding sequence under control of a promoter and any other suitable sequences regulating expression. Typical such vectors are plasmids, but other vectors such as phagermids, cosmids, viral vectors and the like can be used according to the nature of the host.

Of course, one or more of the separate vectors may result in integration of the relevant expression systems into the chromosome of the host.

Neither have microbial hosts generally, such as $E.$ $coli$ and yeast, been used successfully to construct polyketides. It is believed that this is due to the lack of holo ACP synthase which, according to the methods of the invention, can be supplied to these hosts.

Thus, in order to produce the polyketides of the invention, suitable hosts are modified to contain vectors, typically plasmids, which contain expression systems for the production of proteins with one or more of the activities associated with PKS. By placing various activities on different expression vectors, a high degree of variation can be achieved. A variety of hosts can be used; any suitable host cell for which selection markers can be devised to assure the incorporation of multiple vectors can readily be used. Preferred hosts include yeast, *E. coli*, actinomycetes, and plant cells, although there is no theoretical reason why mammalian or insect cells or other suitable recombinant hosts could not be used. Preferred among yeast strains are *Saccharomyces cerevisiae* and *Pichia pastoris*. Preferred actinomycetes include various strains of Streptomyces.

The choice of hosts, of course, dictates the choice of the control sequences associated with the expression system as well as the selectable markers. Suitable promoter systems, for example, for use in *E. coli* include the tryptophan (trp) promoter, the lactose (lac) promoter, the T7 promoter and the λ-derived $P_L$ promoter and N-gene ribosome binding site. For yeast, suitable control sequences include promoters for the synthesis of glycolytic enzymes, such as 3-phosphoglycerate kinase. Other promoters include those for alcohol dehydrogenase (ADH-1 and ADH-2), isocytochrome-C, acid phosphatase, degradative enzymes associated with nitrogen metabolism and enzymes responsible for maltose and galactose utilization. It is also believed that terminator sequences are desirable at the 3' end of the coding sequences.

Suitable promoters for use in mammalian cells, actinomycetes, plant cells, insect cells and the like are also well known to those in the art.

Selectable markers suitable for use in bacteria such as *E. coli* and actinomycetes generally impart antibiotic resistance; those for use in yeast often complement nutritional requirements. Selectable markers for use in yeast include, but are not restricted to URA3, LEU2-d, TRP1, LYS2, HIS1, HIS3. Selectable markers for use in actinomycetes include, but are not restricted to those for thiostrepton-, apramycin-hygromycin-, and erythromycin-resistance.

Methods and materials for construction of vectors, transformation of host cells and selection for successful transformants are well understood in the art.

Thus, according to one embodiment of the invention herein, a single host cell will be modified to contain a multiplicity of vectors, each vector contributing a portion of the synthesis of a PKS system. In constructing multiple vectors for production of aromatic PKS systems, the separate reading frames such as those shown in FIG. 1 may be incorporated on separate vectors or, if properly constructed, portions of reading frames can be distributed among more than one vector, each with appropriate sequences for effecting control of expression. For modular systems a single module or more than one module may reside as a part of an expression system on a single vector; multiple vectors are used to modify the cell to contain the entire desired PKS system.

As stated above, one or more of the expression systems introduced into the host may be integrated into the chromosome.

Thus, to prepare the libraries of the invention, suitable host cells are transformed with the desired number of vectors; by using different selectable markers on each vector desired as part of the modification, successful transformants which are modified by inclusion of all the desired vectors can be selected. By using mixtures of a first vector with a first selectable marker containing a multiplicity of expression systems for a portion of a PKS synthase, and a mixture of a second vector with expression systems for a variety of a second portion of a PKS system, and so forth, colonies of successful transformants are obtained that have a combinatorial representation of "hybrid" PKS systems. By preparing panels of individual colonies of such successful transformants, a library of PKS systems is obtained and thereby a library of polyketides. An expression system for holo ACP synthase is also supplied if needed. The polyketides may be glycosylated depending on the nature of the host.

This approach can also be modified by effecting the integration of the appropriate portion of one or more of the multiple vectors into the chromosome of the host. Integration can be effected using suitable phage vectors or by homologous recombination. If homologous recombination is used, the integration may also delete endogenous PKS activity ordinarily residing in the chromosome, as described in the above-cited PCT application WO 95/08548. In these embodiments, too, a selectable marker such as hygromycin or thiostrepton resistance will be included in the vector which effects integration.

The libraries of polyketides can then be screened for activity with respect to any polyketide responsive target in order to identify particular polyketide members that will activate or otherwise bind to the target. Such screening methods are standard in the art.

In a particularly preferred embodiment of the invention, the library can be made self-screening by introducing a polyketide-responsive receptor that is intracellular to or is displayed at the surface of the host cell producing the polyketide itself. This "autocrine" system allows the colonies to self-select for those activating the receptor. Such systems are described, for example, in an article by Broach, J. R. and Thorner, J., *Nature* (1996) 384:Supp.7:14–16.

Autocrine systems need not be limited, however, to receptors, but can include proteins that are expressed internal to the cell and whose interaction can be evaluated with respect to the polyketides produced, in a manner analogous to the yeast 2 hybrid system described by Fields in U.S. Pat. No. 5,283,173.

Thus, the cells are modified to create "cell-based detection systems for polyketide function." The function of the polyketide may include agonist or antagonist activity with respect to a receptor which is either produced at the surface of the cell or produced intracellularly, or the polyketides may be agonists or antagonists for two hybrid 5 interaction screens so that it will be possible to select for protein-protein interaction inhibitors or cross-linking factors analogous to rapamycin and FK506.

It should be noted, that such cell-based detection systems are also useful in screening libraries of polyketides which are produced from cells containing only single vector systems. Thus, these improvements are applicable not only to the multivector combinatorial libraries of the present invention but also to polyketide synthase and polyketide libraries produced using cells containing these systems on a single expression vector.

As mentioned above, additional enzymes which effect post translational modifications to the enzyme systems in the PKS may need to be introduced into the host through suitable recombinant expression systems. In addition, enzymes that activate the polyketides themselves, for example, through glycosylation may be needed. It may also be necessary to modify the catalytic domains to alter their substrate specificity or to substitute domains with the appropriate specificity. For example, it is generally believed that malonyl CoA levels in yeast are higher than methylmalonyl CoA; if yeast is chosen as a host, it may be desirable to include catalytic domains that can utilize malonyl CoA as an extender unit, such as those derived from spiramycin or tylosin.

Figure 4:
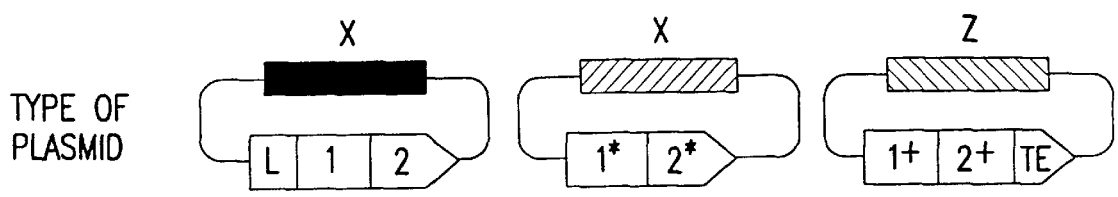
FIG. 4 is a diagram which shows the conceptualization of a multivectored modular PKS system.

FIG. 4 diagrams one embodiment of the conceptual basis of the present invention wherein three sevarate vectors are employed to produce a modular PKS. As shown, each vector permits the construction of 64 different open reading frames using two extender ATs (one from methylmalonyl CoA and the other from malonyl CoA) and the four combinations involving KR, DH, and ER as described above. Thus, module No. 1 may employ malonyl CoA as an extender unit; module No. 2 methylmalonyl CoA; the opposite sequence can be used, or both extenders might use malonyl CoA or both might use methylmalonyl CoA. This results in four separate types of extender combinations, each of which is multiplied by the four KR/DH/ER variants. Each separate plasmid offers the same set of possibilities; one of the plasmids must also contain a loading function and one must contain a thioesterase function. Thus, by construction of 192 plasmids, the upper limit of synthesis of novel polyketides is 64×64×64 or 262,144 molecules, providing an efficient method to obtain large numbers of novel polyketides.

Figure 5:
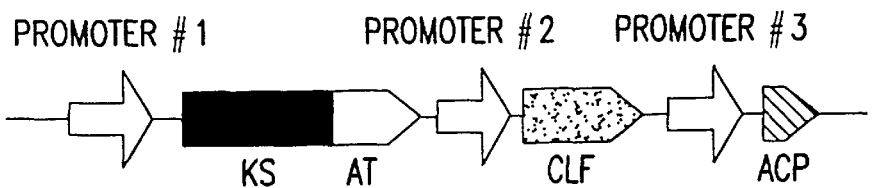
FIG. 5 is a diagram of a multivectored aromatic PKS system.

FIG. 5 shows an approach to a multiple vector aromatic PKS that is set forth in greater detail in Example 11 hereinbelow. In FIG. 5, the three separate reading frames of a typical aromatic polyketide synthase are placed on separate vectors. Thus, each reading frame can be derived from a different aromatic polyketide synthase if desired.

Another modification useful in varying the polyketides produced regardless of the host cell employed manipulates the PKS, in particular a modular or fungal PKS, to inactivate the ketosynthase (KS) on the first module. This permits enhanced efficiency in permitting the system to incorporate a suitable diketide thioester such as 3-hydroxy-2-methyl pantonoic acid-N-acetyl cysteamine thioester, or similar thioesters of diketide analogs, as described by Jacobsen et al. *Science* (1997) 277:367–369. The construction of PKS modules containing inactivated ketosynthase regions is described in U.S. Pat. No. 6,080,555 and published in PCT application W097/02358 incorporated herein by reference. These modified PKS modules can be employed in the various embodiments of the invention in preparing libraries using multivector methods and/or in *E. coli* and yeast-based production organisms for the polyketides which may require the additional expression of a gene encoding a suitable holo-ACP synthase.

Thus, the present invention provides the opportunity to produce polyketides in hosts which normally do not produce them, such as *E. coli* and yeast. The invention also provides more efficient means to provide a variety of polyketide products by supplying the elements of the introduced PKS, whether in an *E. coli* or yeast host or in other more traditionally used hosts, on multiple separate vectors. The invention also includes libraries of polyketides prepared using the methods of the invention.

Uses of Polyketides

As is well understood, the polyketides, in their glycosylated forms, are powerful antibiotics. In addition, many polyketides are immunosuppressants and anticancer agents. It has also been found that polyketides or their glycosylated forms can reduce inflammation under certain circumstances. This is believed to be due to the ability of certain antibiotics to inhibit the release of cytokines such as IL-8. For example, Hott, M. in the *Kurume Medical Journal* (1996) 43:207–217 concludes that the favorable clinical effect of erythromycin in cryptogenic organizing pneumonia and related conditions is due to inhibition of neutrophil accumulation in the peripheral airways through local suppression of IL-8 production. In further experimental work, Tamaoki, J. et al *Antimicrobial Agents and Chemotherapy* (1996) 40:1726–1728 showed that pretreatment of guinea pigs with roxithromycin or erythromycin inhibited the increase in goblet cell secretion when IL-8 was inhaled. Hamada, K. et al. *Chemotherapy* (1995) 41:59–69 showed that the antitumor effect of erythromycin in mice was due to enhancing the production of IL-4. In another study, Keicho, N. et al., *Journal of Antibiotics* (Tokyo) (1993) 46:1406–1413, state that erythromycin has been reported to depress the extent of inflammation independent of its antimicrobial action and show that erythromycin suppresses the proliferative response of human lymphocytes stimulated with mitogens and antigens but had no effect on concanavilin-A induced IL-2 production or IL-2R-α expression. Bailly, S. et al. *Antimicrobial Agents and Chemotherapy* (1991) 35:2016–2019 showed that roxithromycin, spiramycin and erythromycin have differing effects on production of IL-1α, IL-1β and L-6 as well as tumor necrosis factor α. Spiramycin, and to a lesser extent, erythromycin increase total IL-6 production without affecting IL-1α, IL-1β or TNFα. Roxithromycin had no effect.

Thus, there are a number of papers which indicate that antibiotics are also important in modulating inflammatory mechanisms. The literature appears to show that erythromycin diminishes the production of IL-8, but enhances the production of IL-6, IL-1 and IL-2. Spiramycin has been shown to enhance the production of IL-6.

These examples are intended to illustrate but not to limit the invention.

EXAMPLE 1

Construction of 102d, a 6-MSAS Yeast Expression Vector

Control sequences effective in yeast were obtained and inserted into plasmid pBlueScript (Stratagene) along with a polylinker. The *S. cerevesiae* ADH2 promoter was amplified by PCR using the following primers:

forward: GGGAGCTCGGATCCATTTAGCGGCCG-CAAAACGTAGGGGC (SEQ ID NO:1)

reverse: CCGAATTCTAGAGGTTFCATATGGTAT-TACGATATAGTTAATAG (SEQ ID NO:2).

The forward primer contains 15 bases complementary to the 5' ADH2 sequence and introduces SacI (nucleotides 3–8), BamHI (nucleotides 9–14), and NotI (nucleotides 20–27) restriction sites. The reverse primer contains 15 bases complementary to the 3' ADH2 sequence and introduces NdeI (nucleotides 18–23), XbaI (nucleotides 7–12), and EcoRI (nucleotides 3–8) sites.

The ADH2 terminator was amplified by PCR using the following primers:

forward: GGGAATTCATAGTCGACCGGACCGATGC-CTTCACGATTTATAG (SEQ ID NO:3)

reverse: TTTTCTATTATAAGATGAAAAACGAGGG-GAGCTCCCATGGCC (SEQ ID NO:4).

The forward primer introduces EcoRI (nucleotides 3–8), SaiI (nucleotides 12–17), and RsrII (nucleotides 17–24) restrictions sites. The reverse primer introduces XhoI (nucleotides 29–34) and Asp718 (nucleotides 35–40) restriction sites.

Figure 6:
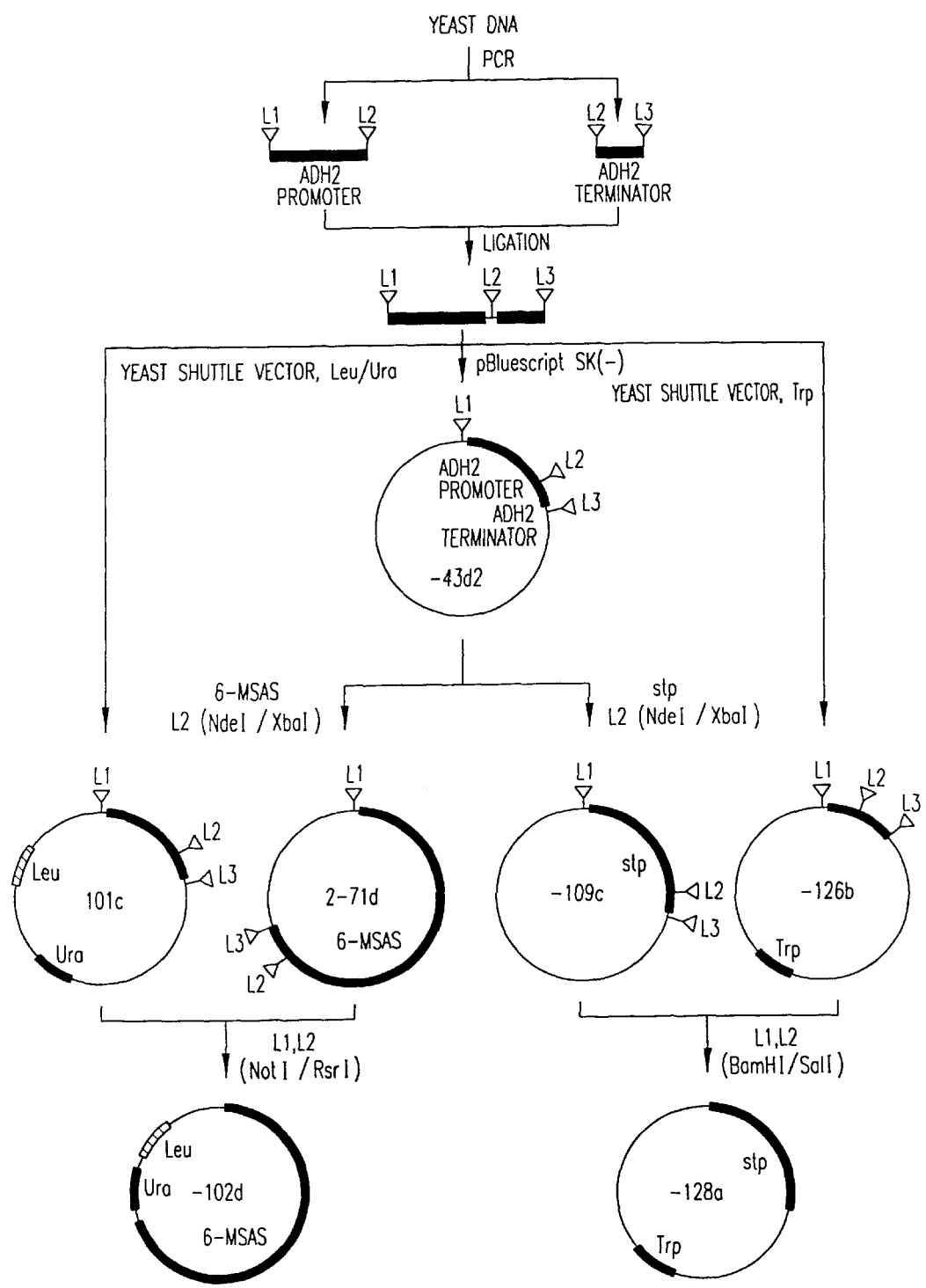
FIG. 6 shows, diagrammatically, the construction of a vector for expression of a holo-ACP synthase and a vector for the expression of the gene encoding 6-MSAS, both vectors for use in yeast.

The SacI/EcoRI fragment containing the ADH2 promoter, the EcoRI/Asp718 fragment containing the ADH2 terminator, and the SacI/Asp718 fragment of pBlueScript were ligated to produce an intermediate vector, 43d2 which contains cloning sites (L2) for 6MSAS and the gene for the surfactant phosphopantothein transferase from *B. subtilis* (the sfp gene). See FIG. 6. It also contains sites (L1, L3) for transferring the promoter/terminator cassette into yeast shuttle vectors as well as sites (L1, L2) for moving the promoter/gene cassettes from the intermediate BlueScript vector into the yeast shuttle vector.

The ADH2 promoter/terminator was then introduced into the *E. coli*/yeast shuttle vector pYT (a gift from Dr. S. Hawkes, University of California, San Francisco). The 13.2-kbp BamHI/SalI restriction fragment from pYT was ligated to the 757-bp BamHI/XhoI restriction fragment from 43d2 to yield plasmid 101c, which contains Leu and Ura markers for selection.

To complete construction of the expression vector, a 5.3-kbp NdeI/XbaI restriction fragment containing the gene for 6-methylsalicylic acid synthase (6-MSAS) from *Penicillium patulum* was obtained from demethylated plasmid pDB 102 (Bedford, D., et al., *J Bacteriology* (1995) 177:4544–4548) and ligated into NdeI/XbaI-restricted 43d2, yielding intermediate plasmid 71d. The 6.1-kbp NotI/lRsrII restriction fragment from 71d was ligated to the 12.6-kbp NotI/RsrII restriction fragment from 101c to produce the expression vector 102d.

EXAMPLE 2

Expression of 6-MSAS in *Saccharomyces cerevesiae*

Competent *Saccharomyces cerevesiae* InvSc1 (MATa his3D1 leu2 trpl-289 ura3-52) (Invitrogen) was transformed with 102d, then plated on minimal agar plates (1.7 g/L yeast nitrogen base without amino acids or ammonium sulfate (DIFCO), 5 gL $(NH_4)_2SO_4$, 20 g/L glucose, 20 g/L agar containing amino acids for selection based on uracil prototrophy. Transforrnants were picked and grown for 24 hours in uracil-deficient minimal medium. Plasmid DNA was isolated from the transformants and analyzed by restriction digestion analysis to confirm identity.

A successful transformant was used to inoculate 2 mL of uracil-deficient minimal medium and was grown overnight at 30° C. on an orbital shaker. A 100-uL aliquot of this culture was used to inoculate 10 mL of YPD medium (Wobbe, C. R., in *Current Protocols in Molecular Biology*, Supplement 34:13.0.1–13.13.9 (Wiley, 1996)) (10 g/L yeast extract, 20 g/L peptone, 20 g/L glucose), and the culture was grown at 30° C. on a shaker.

Cells were collected by centrifugation of 500 uL-aliquots of the culture taken after 18 and 36 hours of growth and lysed by boiling in 50 uL of 2×SDS gel loading buffer for 2 minutes.

The cell lysates were analyzed by loading onto 12% SDS-PAGE gels. A band corresponding to the expected size of 6-MSAS was observed at ca. 190 kD.

EXAMPLE 3

Construction of a Holo ACP Synthase Expression Vector

The *Bacillus subtilis* sfp gene encodes a holo ACP synthase, i.e., a phosphopantetheinyl transferase, and is inserted into plasmid YepFLAG-1 (IBI/Kodak).

The 5.7-kbp PacI/NotI restriction fragment of YepFLAG-1 was ligated with a synthetic polylinker to introduce the following restriction sites:

(PacI)-BamHI-NotI-NcoI-RsrII-XhoI-SalI-(NotI).

The original PacI and NotI ligation sites were destroyed in the ligation. The resulting vector was cut with BamHI and SalI and was ligated to BamHI/XhoI-digested 43d2 (see Example 1) to introduce the ADH2 promoter/terminator, thus obtaining the plasmid 126b. The *Bacillus subtilis* sfp gene was amplified from the plasmid pUC8-sfp (Nakano, M. et al. *Mol Gen Genet* (1992) 232:313–321) by PCR using the primers:

forward: TAGACACATATGAAGATTTACGGAATT-TATATG (SEQ ID NO:5)

reverse: TACATTCTAGAAATTATAAAAGCTCTTCG (SEQ ID NO:6).

The forward primer introduces a NdeI restriction site (nucleotides 7–12) and the reverse primer introduces an XbaI site (nucleotides 6–11).

The resulting PCR fragment was ligated into the NdeI and XbaI sites of 43d2 to produce plasmid 109c.

The 1.3-kbp BamHI/SalI restriction fragment of 109c was ligated to BamHI/SalI-digested 126b to produce expression vector 128a which contains the sfp gene under control of the ADH sequences and tryptophan prototrophy as selection marker.

EXAMPLE 4

Production of 6-methylsalicylic Acid in Yeast

Competent *Saccharomyces cerevesiae* InvSc1 cells were transformed with 102d (6 MSAS) and 128a (sfp holo ACP synthase). 128a was used in the first transformation with selection for tryptophan prototrophy; a successful transformant was then transfected with 102d, with selection for tryptophan and uracil prototrophy. Transformants appeared after 48–72 hr at 30° C.

Single colonies of the 6 MSAS/sfp transformants were grown 24–48 hr at 30° C. in tryptophan- and uracil-deficient minimal medium, after which 100 µl was used to inoculate 10 µl of YPD medium. Cultures were grown for 18 hr at 30° C. in an orbital shaker at 225 rpm. YPD medium (50 ml) was inoculated with 0.5 ml of the overnight cultures and incubated at 30° C. for 142 hr. One ml aliquots were removed periodically and the cells were collected by centrifugation. The cells were suspended in SDS-PAGE loading buffer, boiled for 2 min and subjected to SDS-PAGE to determine the production of the PKS protein. The supernatants were analyzed for 6-methylsalicylic acid production by injection of 20 uL onto an HPLC (C18 reverse-phase column, water/acetonitrile/acetic acid gradient, diode-array UV detection). The LC parameters were as follows: Solvent A=1% acetic acid in water; Solvent B=1% acetic acid in acetonitrile; gradient=20% B to 80% B in 30 min then to 100% in 2 min; flow rate=0.5 ml/min. The amount of 6-methylsalicylic acid was quantitated by peak integration at 307 nm. A standard curve was generated using authentic 6-methylsalicylic acid (Seidel, J. L., et al., *J Chem Ecology* (1990) 16:1791–1816).

Figure 7:
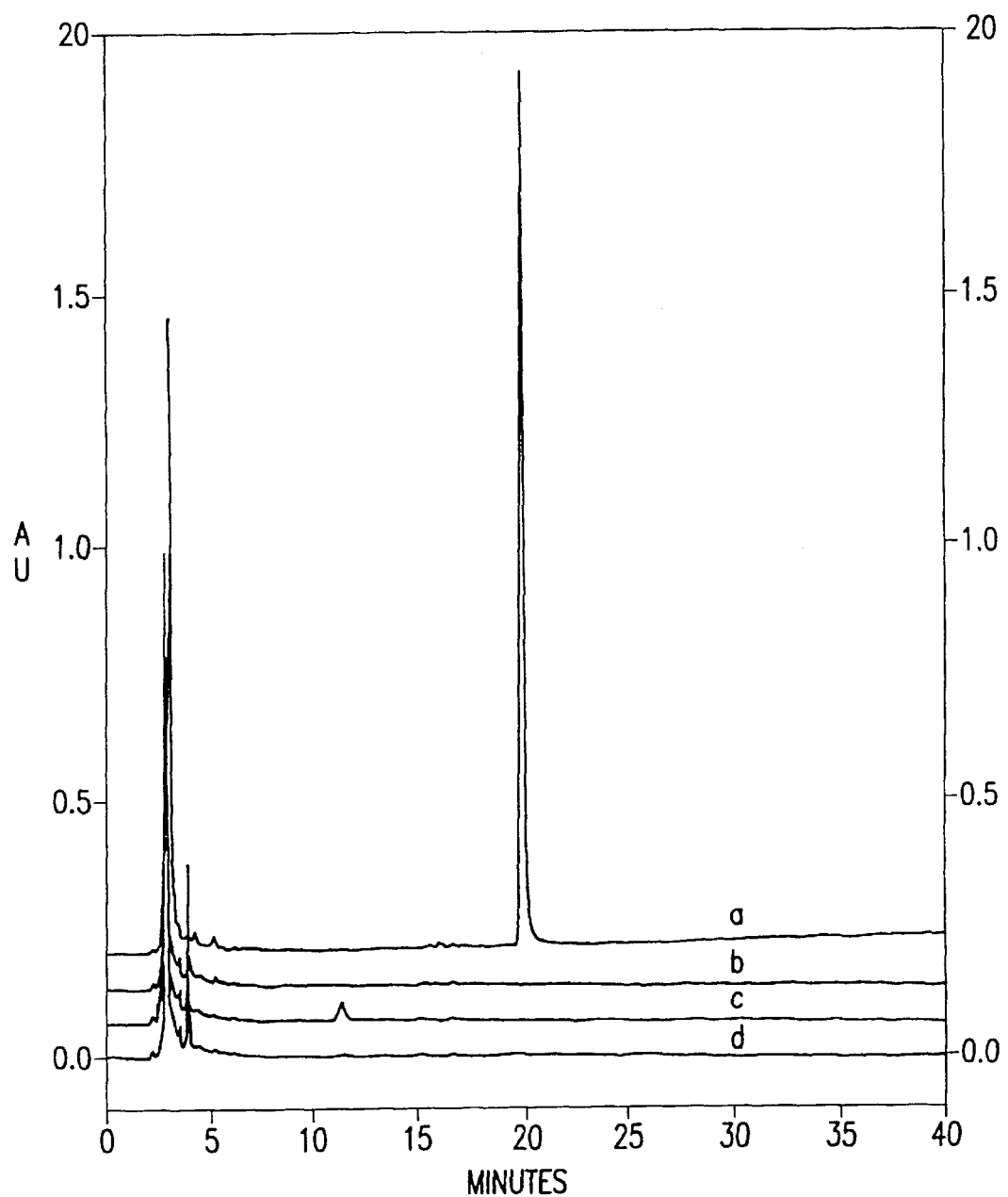
FIG. 7 shows the results of HPLC run on supernatants of yeast cultures transformed with various vectors of the invention.

The results of a typical experiment are shown in FIG. 7. Yeast which contained only the control plasmid O1c or control plasmid and the sfp expression plasmid 128a produced no 6-MSA (trace b, d). Yeast containing only the 6-MSAS expression vector 102d produced a barely detectable amount of 6-MSA (trace c). Yeast containing both the 6-MSAS expression vector 102d and the sfp expression vector 128a produced as much as 1.7 g/l of 6-MSA (trace a).

Figure 8A:
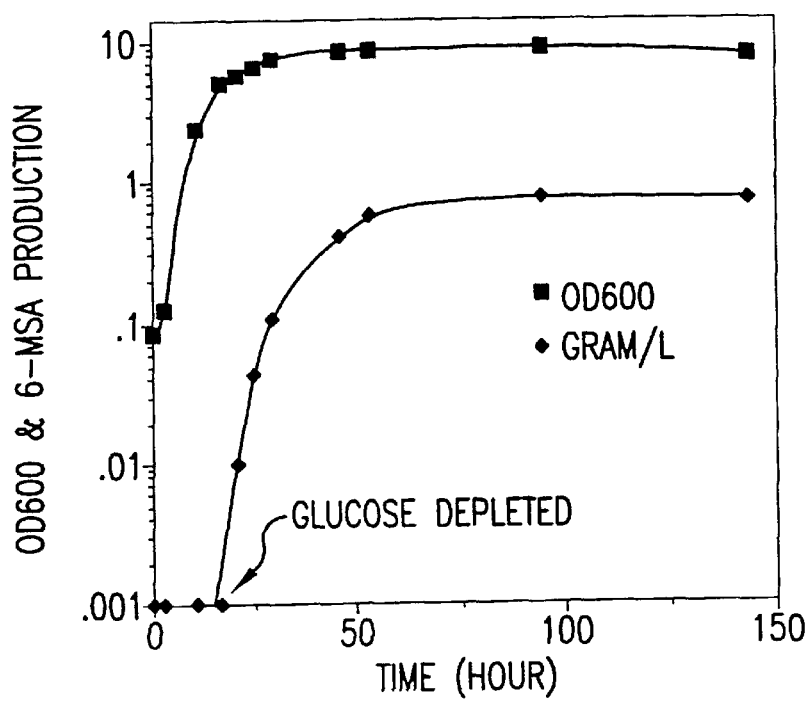
FIGS. 8A and 8B show the kinetics of production of the antibiotic 6-methyl salicylic acid (6-MSA) in yeast (FIG. 8A) and in *E. coli* (FIG. 8B).

The kinetics for yeast growth and 6-MSA production for the transformant are shown in FIG. 8A. As shown, the open squares represent growth as measured by $OD_{600}$. The closed circles represent the production of 6-MSA in g/L. The production of 6-MSA begins when glucose is depleted consistent, with derepression of the ADH2 promoter. A plateau was reached after about 60 hr of growth and remained constant up to 150 hr.

For large-scale preparation of 6-MSA, a 500 ml yeast culture harboring the two plasmids was grown for 120 hr and the cells were removed by centrifugation. The supernatant broth (280 ml) was acidified with 28 ml glacial HOAc, then extracted with 280 ml ethyl acetate. The organic extract was concentrated to dryness under reduced pressure. The crude product was purified by crystallization from water and the crystals were dried under vacuum over KOH. The identity of 6-MSA was confirmed by NMR and mass spec. In the specific experiment described above, the 280 ml of cell-free yeast culture yielded 240 mg of 6-MSA as crystalline needles. Shake flask cultures typically produced over 1 g/L of 6-methylsalicylic acid.

EXAMPLE 5

Construction of the DEBS Module 6 KR-ACP-TE Expression Vector, Plasmid 104

The plasmid, 90, which contains a T5 promoter, 2 lac operators, and lac$^{1q}$ qwas constructed by ligating a 1.1-kbp XhoI/XbaI fragment of pQE60 (Qiagen) to the larger XhoI/XbaI fragment of pET22b(+) (Novagen). A PstI/EcoRI restriction fragment containing the DNA encoding module 6 KR-ACP-TE was ligated into plasmid 90 to give plasmid 104, an expression vector for this module.

EXAMPLE 6

Phosphopantetheinylation of Module 6 KR-ACP-TE

A. In vivo:

The β-alanine auxotroph *Escherichia coli* SJ16 (*E. coli* Genetic Stock Center), was cotransformed with 104 and a holo-ACP synthase expression plasmid containing genes for either:

*E. coli* fatty acid synthase holo-ACPS (ACPS);

*E. coli* enterobactin synthetase holo-ACPS (EntD), or

*Bacillus brevis* gramicidin synthetase holo-ACPS (GsP).

Holo-ACPS expression plasmids were generous gifts of Dr. Daniel Santi, UCSF (Ku, J., et al., *Chemistry & Biology* (1997) 4:203–207).

Each cotransforrnant was grown in minimal medium E (Vogel, H. J. et al., *J Biol Chem* (1956) 218:97–106) supplemented with 0.001% thiamine, 0.01% methionine, and 100 uM β-alanine at 37° C. for 20 h. Cells were collected by centrifugation and washed with 1 mL of growth medium without β-alanine. This wash was repeated four times. Finally, the cells were incubated in 1 mL of growth medium without β-alanine at 37° C. for 6 h.

A 30-uL aliquot of the starved cells was added to 1 mL of growth medium supplemented with 0.52 uM [3H]-β-alanine (1 uCi, American Radiolabeled Chemicals, Inc.). After 6 h at 37° C., the cells were induced by addition of IPTG to 1 mM, kept for an additional 3 h at 37° C., and centrifuged. The cell pellet was boiled in SDS gel loading buffer, then analyzed on a 10% SDS-PAGE gel. The gel was stained with Coomassie Blue, photographed, soaked in Amplify (Amersham), dried, and autoradiographed using Kodak Bio-MAX film for 2 days.

The module 6 KR-ACP-TE fragment of DEBS was efficiently labeled upon coexpression with GsP and with EntD, while no labeling was observed upon coexpression with ACPS. The inability of ACPS to activate the DEBS fragment is expected based on the known inactivity and lack of phosphopantetheinylation of the DEBS protein when expressed in *E. coli* (Roberts et al. *Eur J Biochem* (1993) 214:305–311).

B. In vitro:

The module 6 KR-ACP-TE fragment of DEBS was purified from *E. coil* transformed with p104 using a Ni$^{+2}$ affinity column following manufacturer's directions (Invitrogen). Purified surfactin synthetase holo-ACPS (sfp) from *Bacillus subtilis* was a gift of Dr. Christopher Walsh (Harvard Medical School). Labeled 3H-coenzyme A was a gift of Dr. Daniel Santi (UCSF).

All assays were performed in 10 mM MgCl$_2$, 50 mM Tris-HCl (pH 8.8), in a total volume of 100 uL, and contained 40,000 cpm of 3H-coenzyme A and 0.39 uM sfp. A positive control contained 1.8 uM PheAT domain from gramicidin synthetase (Dr. Daniel Santi, UCSF) which is normally pantotheinylated by sfp. Reactions were kept 12 h at 37° C., then boiled in SDS gel loading buffer and analyzed on a 10% SDS-PAGE gel. The gel was stained with Coomassie Blue, photographed, soaked in Amplify (Amersham), dried, and autoradiographed using Kodak Bio-MAX film for 2 days.

Both PheAT and the module 6 KR-ACP-TE fragment of DEBS were efficiently labeled by sfp.

EXAMPLE 7

Production of 6-methylsalicylic acid in *Escherichia coil*

The plasmid 90 (see Example 5) was converted to p95 by inserting a linker between the EcoRI/HindIII in plasmid 90 so as to introduce restriction sites NdeI and SpeI adjacent to the T5 promoter. The 6-MSAS expression vector, 109, was constructed by ligating a NdeI/XbaI fragment containing the 6-MSAS open reading frame (Pfeifer, E. et al. *Biochemistry* (1995) 34:7450–7459) with the large NdeI/SpeI fragment of 95 leaving about 1 kbp of the linker between the SpeI and HindIII sites of the vector.

The sfp expression vector, 108, was made by ligating a 1.1-kbp EcoRI/PvuII restriction fragment of pUC8-sfp (see Example 3) to pACYC-184 (New England Biolabs) cut with EcoRV after fill-in of the EcoRI site by DNA polymerase I. The orientation of the sfp gene with respect to the promoter was verified by HindIII digestion.

Plasmids 108 and 109 were cotransformed into *E. coli* C2453, and transformants were selected by chloramphenicol and ampicillin resistance. A single colony containing both plasmids was grown in ATCC medium 765 supplemented with 10% glycerol at 37° C. to a density of 1.0 OD$_{600}$ then cooled to 30° C. and induced by addition of 0.5 mM IPTG. Cell growth was continued for 36 hr at 30° C. Protein expression was checked by 10% SDS-polyacrylamide gel. The formation of 6-methylsalicylic acid was followed by HPLC analysis of the culture broth.

The concentration of 6-MSA was estimated as described in Example 4 from a plot of concentration vs integrated area of corresponding HPLC peak using an authentic sample. The identity of the product was confirmed by LC-mass spectroscopy, which revealed [M+H]+=153, with a major fragment at m/z=135 corresponding to loss of H$_2$O. Under these conditions, the culture produced 50 mg/L of 6-methylsalicylic acid.

Figure 8B:
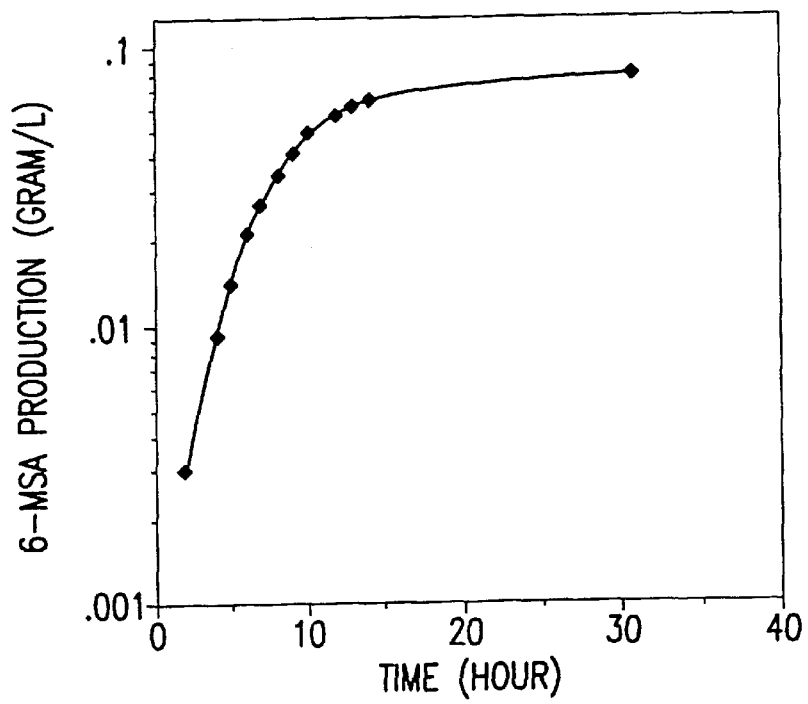

The production of 6-MSA in *E. coil* was dependent on the presence of the plasmid encoding the sfp protein. *E. coil* transformed with only the 6-MSAS expression vector, 109, when induced by IPTG followed by incubation at 37° C. for 4 hr, showed production of the approximately 190 kD 6-MSAS at about 5% of total protein. However, most of the protein was insoluble and 6-MSA was not detected in the medium. When the β-alanine auxotroph *E. coil* SJ16 containing the 6-MSAS expression vector 109 was incubated with labeled β-alanine before and after induction, no radioactivity was found in the 6-MSAS band on SDS-PAGE; thus, it appears the 6-MSAS was not modified with the phosphopantetheinyl cofactor by endogenous transferase. In a similar experiment involving *E. coli* SJ16 cotransformed with both plasmid 108 and 109, a detectable amount of radioactivity was found in the 190 kD 6-MSAS band; however, no 6-MSA was detected under these conditions. However, when the temperature of incubation was lowered to promote proper protein folding and glycerol was added to the medium to increase levels of intracellular malonyl CoA substrate, production of 6-MSA was improved. Thus, when cells were grown at 30° C. in the absence of glycerol or at 37° C. in the presence of 10% glycerol, no 6-MSA was produced. However, when grown as described above at 30° C. in the presence of 10% glycerol, 6-MSA was produced up to about 75 mg/L after 24 hr of incubation. The kinetics of production are shown in FIG. 8B.

EXAMPLE 8

Production of 6-methylsalicylic Acid in *Saccharomyces cerevesiae* Using a PKS-holo ACP Synthase Fusion Protein A fusion protein between the *Penicillium patulum* 6-methylsalicylic acid synthase (6-MSAS) and the *Bacillus subtilis* surfactin holo ACP synthase (sfp) is made as follows: A 5.3-kbp NdeI/HindIII fragment containing the 6-MSAS gene (see Example 1) is ligated with a 708-bp HindIII/XbaI fragment containing the sfp gene (see Example 3) and with NdeI/XbaI-restricted 43d2 (see Example 1) to produce intermediate plasmid 69.

A ca. 6-kbp NotI/RsrII restriction fragment from 69 is ligated with NotI/RsrII-restricted 101c (see Example 1) to yield the yeast expression vector 26a1 (see Example 1). This vector contains the 6-MSAS/sfp fusion gene between the ADH2 promoter/terminator pair.

The resulting fusion protein consists of connecting the C-terminal lysine of 6-MSAS with the N-terminal methionine of sfp using an (alanine)$_3$ linker, such that the DNA sequence of the gene in the region of the fusion is:

5'-AAGCTTGCC<u>AAA</u>-GCCGCCGCC-<u>ATG</u>AAGATTTAC-3' (SEQ ID NO:7) where the lysine and methionine codons are underlined.

Transformation of *S. cerevesiae* InvSc1 with 26a1 and culturing as described in Example 3 results in production of 6-methylsalicylic acid at a level comparable with that resulting from expression of 6-MSAS and sfp as separate genes. The fusion protein thus combines the enzymatic activities of 6-MSAS and of sfp, self phosphopantetheinoylates, and produces polyketide product.

This is especially useful for transformation of hosts where the number of plasmid replicons useable for expression vectors is limited, where polycistronic messages are not properly processed, or where transformation with multiple vectors is difficult and/or time-consuming.

EXAMPLE 9

Production of 6-deoxyerythronolide B by Mixed Chromosomal/Plasmid Expression Systems in *Streptomyces lividans* Using Chromosomal Integration To demonstrate the feasibility of dividing the three DEBS genes between chromosomal and plasmid expression systems, two experiments were performed. In both experiments, the integrating vector pSET152 (Bierman, M., et al., *Gene* (1992) 116:43–49) was used to place one gene of the DEBS gene cluster under control of the actinorhodin promoter onto the Streptomyces chromosome at the phage attachment site.

The remaining genes were placed onto the replicating plasmid, pRM5 (McDaniel et al., *Science* (1993) 262:1546–1550), also under control of the actinorhodin promoter.

A. The eryAIII gene (encoding modules 5 atid 6 and the thioesterase of DEBS) under control of the actinorhodin promoter was cloned into pSET 152. The resulting vector was used to transform *S. lividans* K4-114, a strain in which the actinorhodin gene has been deleted by homologous recombination by standard methods (U.S. Pat. No. 5,672, 491 incorporated herein by reference). Apramycin-resistant transformants were selected.

An expression plasmid was constructed by clonmg the eryAI and eryAII genes (containing modules 1+2 and 3+4, respectively) into the PacI/EcoRI sites of pRM5 so that the two genes were under the control of the actinorhodin promoter. This plasmid was used to transform protoplasts of the *S. lividans* clone containing the integrated eryAIII gene, and colonies resistant to both thiostrepton and apramycin were selected.

B. Alternatively, the actinorhodin promoter and the eryAI gene were cloned into pSET152 and subsequently integrated into the *S. lividans* chromosome. The eryAII and eryAIII genes were cloned into pRM5 behind the actinorhodin promoter, and this plasmid was used to transform the *S. lividans* strain containing the integrated eryAI gene.

Randomly selected colonies of the above organisms containing mixed chromosomal-plasmid expression systems were cultured on R2YE medium over XAD-16 resin, and ethanol extracts of the resin collected after 7 days were analyzed for production of 6-deoxyerythronolide B by LC/mass spectrometry. Cultures from both experiments A and B produced 6-deoxyerythronolide B at levels of 15–20 mg/L, comparable to that found in extracts of cultures of *S. lividans* containing pCK7, a replicating plasmid containing all three eryA genes under control of the actinorhodin promoter.

EXAMPLE 10

Production of 6-deoxyerythronolide B by Mixed Chromosomal/Plasmid Expression systems in *Streptomyces lividans*

An alternative method for constructing a mixed chromosomal-plasmid expression system for multi-gene PKSs also achieves simultaneous creation of a clean host for polyketide production. A suitable expression host, which normally produces a polyketide product, has its chromosomal PKS genes replaced by a subset of the foreign PKS genes through homologous recombination. This accomplishes the desired chromosomal integration of the foreign PKS genes while simultaneously eliminating interference from and competition by the native PKS. The example is readily illustrated for *S. coelicolor* and *S. lividans*, both of which make the blue polyketide actinorhodin.

A method by which the entire actinorhodin gene cluster is removed from these organisms and replaced with an antibiotic marker through homologous recombination has been described (U.S. Pat. No. 5,672,491). This method is adapted as follows: The recombination vector consists of any vector capable of generating single-stranded DNA (e.g., pBlueScript) containing the following elements: 1) a DNA sequence homologous to the 5' 1-kbp end of the act cluster; 2) a resistance marker (e.g., hygromycin or thiostrepton); 3) the act II-orf4 activator gene; 4) the act promoter; 5) one or more genes of the foreign PKS; and 6) a DNA sequence homologous to the 3' 1-kbp end of the act cluster. Transformation of S. coelicolor or S. lividans with the recombination vector followed by selection for hygromycin resistance and screening for loss of blue color provides a host lacking the actinorhodin gene cluster and containing a chromosomal copy of the foreign PKS genes along with the needed actinorhodin control elements. This host is subsequently transformed by replicating vectors (e.g., SCP2*-based plasmids) and/or with integrating phage vectors (e.g., pSET 152) containing other genes of the foreign PKS to complete the set of PKS genes and produce polyketide product.

EXAMPLE 11

Construction of Yeast Vectors for Expression of an Aromatic Minimal PKS

The genes encoding the KS/AT bifunctional protein and the CLF gene of the actinorhodin PKS (diagrammed in FIG. 5) are amplified and tailored by PCR and cloned into the yeast expression vector pYEUra3 (Clontech) under control of the Gal1 and Gal10 promoters respectively. The ACP gene is amplified and cloned together with the holo-ACP synthase gene, if necessary, into a plasmid derived from pYEUra3 by replacement of the Ura3 gene with the Leu2-d gene. Expression is also driven by the Gal1 and Gal10 promoters respectively. Yeast strain BJ2168 is cotransformed with these plasmids and also with plasmid 128a (see Example 3) and transformants selected on a uracil- and leucine-deficient plates by standard methods. Expression is induced by growth in 2% galactose according to the manufacturer's instructions. The polyketide produced by this synthase system is predicted to be

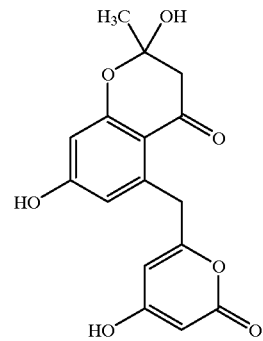

EXAMPLE 12

Construction of Yeast Vectors for Expression of Modular Synthase Activities Two vectors are constructed. One contains the putative two-module system of spiramycin under control of the ADH-2 promoter and colinear with the thioesterase domain of the erythromycin PKS. The coding sequence construct is engineered to be flanked by an NdeI site at the initiation codon and an NsiI site following the termination codon; this construct is cloned using synthetic oligonucleotide linkers into pYT.

Figure 9:
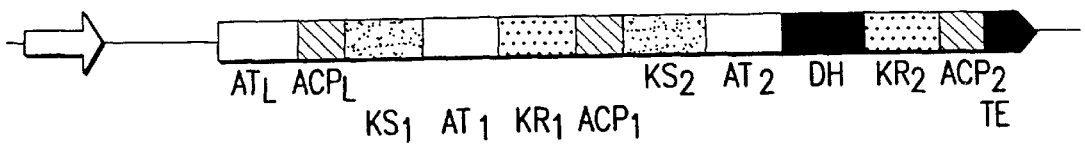
FIG. 9 shows the expression systems for two modular PKS for use in vectors compatible with yeast along with the expected products.
Figure 9:
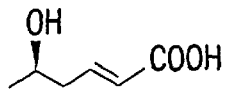
Figure 9:
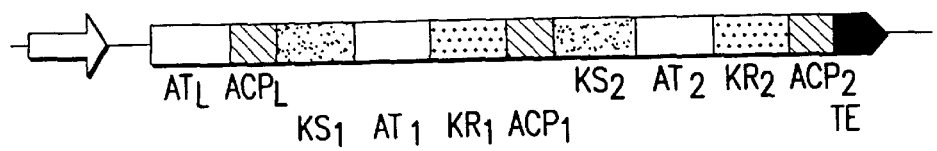
Figure 9:
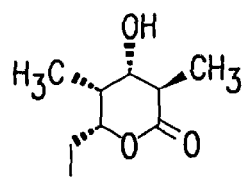

In the second vector, the analogous structure from the erythromycin PKS system flanked by NdeI and NsiI sites as described by Kao, C. et al. *J Am Chem Soc* (1995) 117:9105–9106 is cloned into pYT so as to be placed under control of the ADH-2 promoter. FIG. 9 shows the relevant expression portion of these vectors and the expected polyketide products.

---

What is claimed is:

1. A modified recombinant host cell, which, in unmodified form does not produce polyketides, which cell is modified to contain an expression system for a minimal polyketide synthase (PKS) and an expression system for a holo acyl carrier protein (ACP) synthase, wherein said minimal PKS comprises a ketosynthase (KS) domain, an acyl transferase (AT) domain, and an acyl carrier protein (ACP) domain for a modular PKS or a fungal PKS; and wherein said holo ACP synthase is selected from the group consisting of:

the enterobactin synthetase holo-ACP synthase (EntD) from *Escherichia coli*, the gramacidin synthetase holo-ACP synthase (GsP) from *Bacillius brevis*, and the surfactin synthetase holo-ACP synthase (sfp) from *Bacillius subtilis*.

2. The modified cell of claim 1 which is *E. coli* or yeast.

3. The modified cell of claim 1 wherein said minimal PKS is the synthase for 6-methyl salicylic acid.

4. The modified cell of claim 1 wherein said expression system for said minimal PKS and said expression system for said holo ACP synthase are present on separate vectors.

5. The modified cell of claim 1 wherein at least one of said expression systems is integrated into the host cell chromosome.

6. A method to produce a polyketide, which method comprises culturing modified recombinant host cells, according to claim 1, under conditions wherein said expression systems produce the minimal PKS and holo ACP synthase proteins, and wherein a polyketide is produced.

7. A vector adapted for expression in yeast, which vector comprises:

(a) a selectable marker operable in yeast;

(b) an expression system which comprises the coding region of at least one modular PKS system operably linked to a promoter operable in yeast; and (c) an expression system which comprises the coding region of a holo ACP synthase selected from the group consisting of EntD, GsP, and sfp, which coding region is operably linked to a promoter operable in yeast.

8. A yeast cell modified to contain the vector of claim 7.

9. A method to produce a polyketide synthase, which method comprises culturing a yeast cell, according to claim 8, under conditions wherein expression of the modular PKS and the holo ACP synthase is favored.

10. A vector adapted for expression in *E. coli*, which vector comprises:

(a) a selectable marker operable in *E. coli*;

(b) an expression system which comprises the coding region of at least one modular PKS system operably linked to a promoter operable in *E. coli*; and (c) an expression system which comprises the coding region of a holo ACP synthase selected from the group consisting of EntD, GsP, and sfp, which coding region is operably linked to a promoter operable in *E. coli*.

11. An *E. coli* cell modified to contain the vector of claim 10.

12. A method to produce a polyketide synthase, which method comprises culturing an *E. coli* cell, according to claim 11, under conditions wherein expression of the modular PKS and the holo ACP synthase is favored.

13. A recombinant host cell modified to contain either:

(a) at least three vectors; a first vector containing a first selectable marker and a first expression system and a second vector containing a second selectable marker and a second expression system and at least one additional vector containing an additional selectable marker and an additional expression system, wherein said expression systems, in combination, encode and express a modular PKS comprised of a loading domain and at least six extender modules; or (b) at least two vectors and a modified chromosome, said vectors each containing a selectable marker and an expression system and said modified chromosome containing an expression system, and optionally additional vectors containing additional selectable markers and expression systems, wherein said expression systems contained on said vectors, in combination with said expression systems on said chromosome, encode and express a modular PKS comprised of a loading domain and at least six extender modules;

wherein said extender modules of (a) and (b) are each comprised of a KS domain, an AT domain, and an ACP domain;

and wherein each expression system of (a) and (b) produces at least two extender modules; and wherein said recombinant host cell is further modified to contain an expression system for EntD, GsP, or sfp.

14. The cell of claim 13 which is a yeast cell, an *E. coli* cell, an actinomycete cell or a plant cell.

15. The cell of claim 13 wherein at least two of said extender modules are derived from polyketide synthases that produce different polyketides.

16. The cell of claim 15 wherein at least one module further contains a ketoreductase (KR) domain; or a KR and a dehydratase (DH) domain; or a KR, DH and an enoyl reductase (ER) domain; and/or a thioesterase (TE) domain.

17. A method to produce a polyketide, which method comprises culturing cells, according to claim 13, under conditions wherein said expression systems produce the modular PKS and holo ACP synthase proteins, and wherein a polyketide is produced.

* * * * *

UNITED STATES PATENT AND TRADEMARK OFFICE
CERTIFICATE OF CORRECTION

PATENT NO.   : 6,258,566 B1
DATED        : July 10, 2001
INVENTOR(S)  : Philip J. Barr. Daniel V. Santi, Gary W. Ashley and Rainer Ziermann It is certified that error appears in the above-identified patent and that said Letters Patent is hereby corrected as shown below:

<u>Column 1,</u>
Line 12, insert the following paragraph:
--         STATEMENT OF GOVERNMENT INTEREST
This invention was supported in part by SBIR Grant No. 2R44 GM56575. The United States government has certain rights in this invention. --

Signed and Sealed this

Eighth Day of October, 2002

*Attest:*

*Attesting Officer*

JAMES E. ROGAN
*Director of the United States Patent and Trademark Office*